US008102518B2

(12) United States Patent
Haught et al.

(10) Patent No.: US 8,102,518 B2
(45) Date of Patent: Jan. 24, 2012

(54) ZERO ANGLE PHOTON SPECTROPHOTOMETER FOR MONITORING OF WATER SYSTEMS

(76) Inventors: Roy C. Haught, Independence, KY (US); Gary P. Klinkhammer, Corvallis, OR (US); Frank J. Bussell, Eugene, OR (US)

( * ) Notice: Subject to any disclaimer, the term of this patent is extended or adjusted under 35 U.S.C. 154(b) by 0 days.

(21) Appl. No.: 12/801,684

(22) Filed: Jun. 21, 2010

(65) Prior Publication Data
US 2011/0102790 A1    May 5, 2011

Related U.S. Application Data

(63) Continuation of application No. 12/000,622, filed on Dec. 14, 2007, now abandoned.

(51) Int. Cl.
*G01J 3/51* (2006.01)
*G01N 21/64* (2006.01)

(52) U.S. Cl. .......... 356/73; 356/417; 356/418; 356/419; 250/458.1

(58) Field of Classification Search ..................... 356/73
See application file for complete search history.

(56) References Cited

U.S. PATENT DOCUMENTS 3,734,601 A * 5/1973 Heiss ............................. 356/246
5,304,492 A * 4/1994 Klinkhammer ................. 436/52

* cited by examiner

*Primary Examiner* — F. L. Evans
(74) *Attorney, Agent, or Firm* — Hendricks and Associates; John Tarcza

(57) ABSTRACT

A method and apparatus for monitoring water and other fluid systems is described. The fluid is continually monitored spectrophotometrically by measuring many optical parameters in an in-line, on-line system, which compensates for normal fluid changes while detecting abnormalities.

19 Claims, 2 Drawing Sheets

ZERO ANGLE PHOTON SPECTROPHOTOMETER FOR MONITORING OF WATER SYSTEMS

Figure 1:
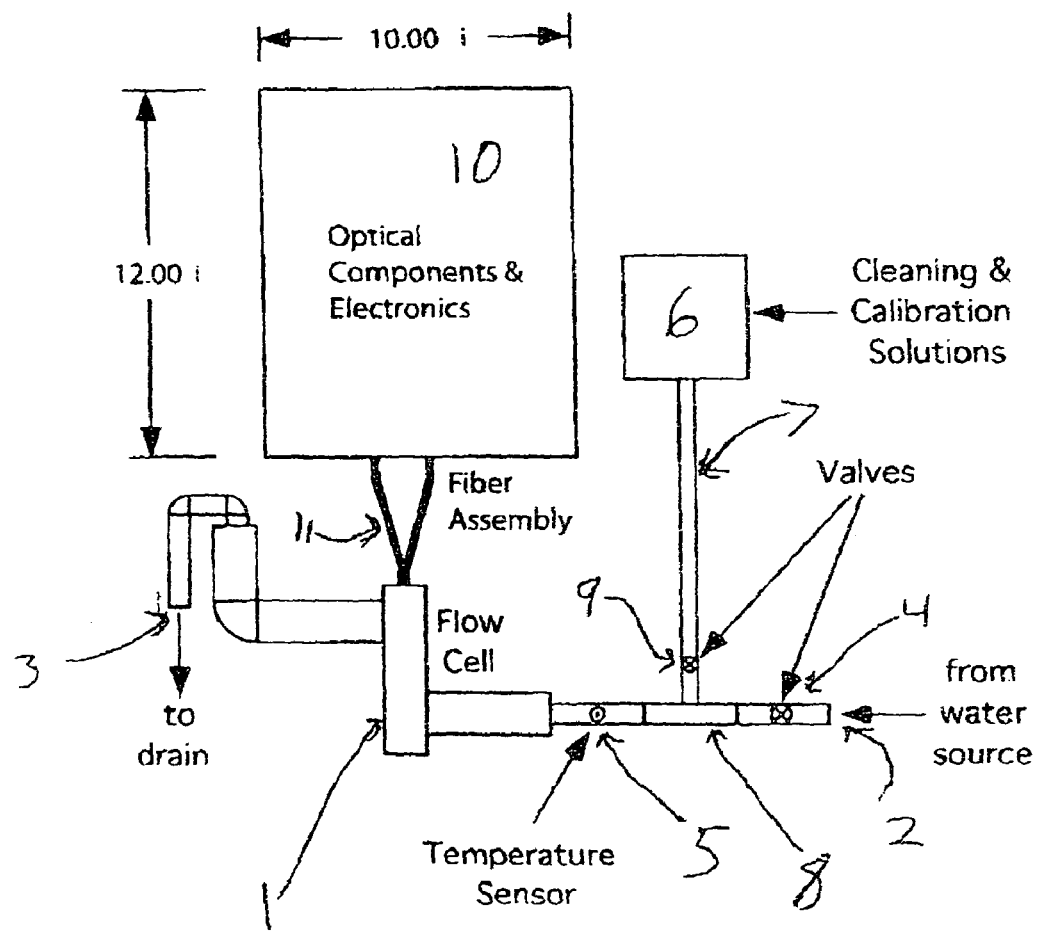

This application is a continuation of U.S. patent application Ser. No. 12/000,622 filed Dec. 14, 2007.

I. FIELD OF THE INVENTION

The present invention relates to a device for continuously monitoring chemical and physical parameters in water.

II. BACKGROUND OF INVENTION

A number of different designs for optically measuring various chemicals and reactions in liquid solutions and suspensions using fiber optics have been proposed over the years.

Designs for fluorescent and other optical measurements using an optical fiber have been proposed in U.S. Pat. Nos. 4,488,814, 4,548,907, 4,564,598, 4,676,640, 4,739,171, 4,929,561, 4,942,303, 5,046,854, 5,595,708, 5,700,428, 5,714,388, 5,757,014, 6,151,111 and 6,597,450. These include single sample sensors and multiwelled multiple sample readers. Similar optical measurements using optical fibers of components in solid objects have been proposed by U.S. Pat. No. 4,650,336. A multichannel probe has also been used in such situations as proposed by U.S. Pat. No. 4,753,530.

Designs for optical instruments for measuring components in fluid flows have been proposed in U.S. Pat. Nos. 4,804,849, 4,973,561, 4,983,038, 5,044,747, 5,304,492, 5,828,458 and 6,888,636.

Designs for multiple optical measurements at multiple locations for various components in fluids using multiple optical fibers have been proposed in U.S. Pat. Nos. 5,491,344, 5,690,894, 5,837,196, 6,146,593 and 6,517,506. These have been used to take various optical measurements.

Computer analysis of the optical output readings has been proposed by many sources including U.S. Pat. No. 4,942,303.

Designs for optical analysis of liquids using multiple fiber optic sensors have been proposed such as U.S. Pat. Nos. 5,997,818, 6,009,339, 6,101,406 and 6,208,880.

Designs for capillary spectrometric analysis of a sample liquid using a fiber optic system has been proposed in U.S. Pat. No. 6,091,490.

Designs for full spectrum analysis of water has been proposed where the "signature" of a particular component in water may be measured. See U.S. Pat. No. 7,027,149.

Waters have been monitored spectrophotometrically for many years. However, generally only one chemical or physical parameter was measured at a time, and measurements were generally made using one chemical technique, such as light scattering for turbidity or fluorescence for chlorophyll-a. Typically, water is monitored sporadically by occasional sampling of retrieved water, which is taken to a laboratory for analysis. Some specialized sensors have been used on water flowing through a pipe, which provide real-time measurement of one component of the water. Generally it is desirable to move laboratory instruments to the field to perform continuous on-line water monitoring but such monitoring has been for a very limited number of water components. Until the present invention, measurement of multiple components using more than one analytical technique has required multiple sensors. This approach requires a skilled operator capable of performing multiple calibration and maintenance procedures. Multiple sensors also propagate errors from each device, which limits the monitoring system's ability to detect anomalies or events using a combination of readings. It is from these problems that the present invention was developed.

III. SUMMARY OF THE INVENTION

The present invention is an integrated spectrophotometric system for monitoring changes in water systems. It is preferably used as an in-line, on-line instrument for monitoring various chemical parameters in a water system on a continuous or intermittent basis such as for water flowing by a monitoring station containing the present invention. This is useful for monitoring natural, drinking, purified or wastewaters from industrial or municipal facilities for routine screening and as an indicator of changes in the water.

Similar to the prior art, the present invention seeks to find anomalies in the fluid flow being tested. From the results, a particular contaminant may be detected, a particular change in how the fluid is handled may be made or reassurance given that the fluid situation is acceptable.

The present invention uses a different technical approach from the prior art. Instead of periodic sampling and analysis or even on line systems which measure only one or a few parameters of the fluid, the present invention uses an integrated spectrometric analysis combining absorption, fluorescence and reflectance techniques to take many (the maximum number is over 100) measurements in real-time along with real-time analysis as fluid is flowing through pipes, troughs etc. The present invention is not simply a collection of old sensors but rather an integrated approach of combining different types of measurements taken from the same sensor.

The present invention also takes absorptive, fluorescent and reflectance measures from the same optical cell, along the same light path and with the same light emitting and detection apparatus. This permits the same instrument to perform many functions.

The present invention further relates to methods and processes for monitoring several parameters with high sensitivity and precision on line while changing valves, etc. automatically in response to anomalies in the fluid stream.

The present invention is further designed to function at high pressures (e.g. up to 100 psi) or temperatures where removing water for sampling is either not practical or disruptive to the process involving the water.

The basic steps of the invention are: taking numerous spectrophotometric measurements, optionally with physical or chemical measurements, analyzing the results individually or by predetermined combinations, adjusting the output based on preloaded algorithms and storing, reporting, or effecting a change based on the results.

The basic apparatus for performing these steps are a flow cell for passing the fluid through, a light emitter, an optical filter, optical fiber connections to and from the flow cell, another optical filter for the resulting light and a detector. These components are selected to give the invention a wide spectrometric capability ranging from 190 to 900 nm.

The present invention is particularly useful for monitoring raw water, wastewater and purified water systems. While the present invention is described in terms of water systems, the same may be applied to any other fluids, which may contain less or no water such as petroleum based products, beverages, foods, solvents, gasses, etc.

III. BRIEF DESCRIPTION OF THE FIGURES

Figure 2:
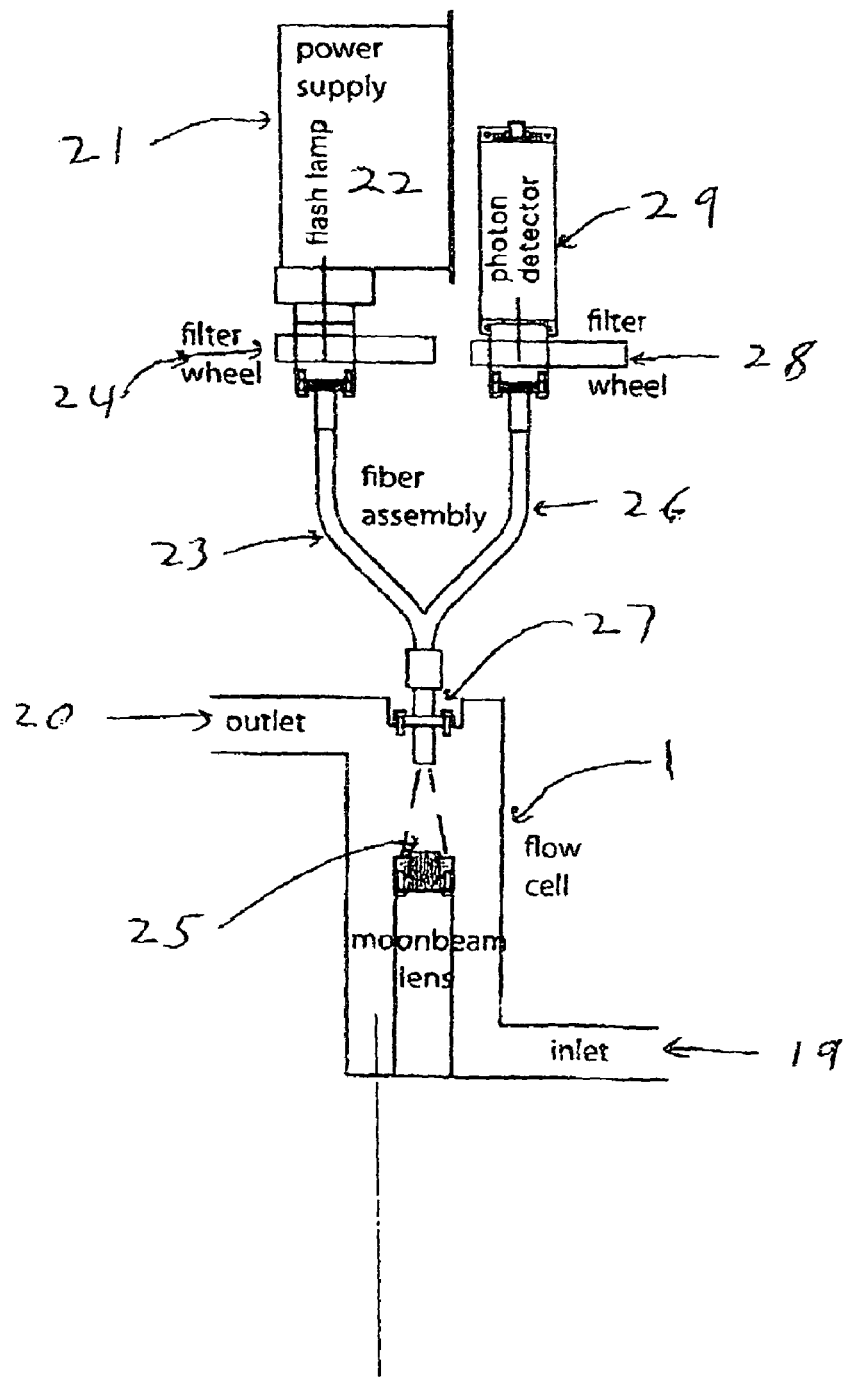

FIG. 1 is a schematic of an in-line sensor system.
FIG. 2 is a closer and more detailed schematic of the optical components in the sensor system.

IV. DETAILED DESCRIPTION OF THE INVENTION

The invention is a fiber optic spectrometer used for in-line, on-line monitoring and remote or off-site monitoring of natural and wastewaters. Unlike prior art this instrument uses a single bifurcated fiber assembly and flow-cell with a reflective lens system to make fluorescence, absorption, and reflectance measurements. The flow-cell and lens system are designed to minimize maintenance and maximize long-term stability. Over 100 discrete measurements could be made which then could be combined with a series of calculated parameters to create a matrix of water quality data. The invention could measure inorganic and organic compounds thus providing an in-depth view of water quality. The invention includes a programmable valve system at the inlet that could be used to automatically select different sample streams, introduce cleaning solutions into the flow-cell, and perform periodic system checks.

In a preferred embodiment, one can make many optical sequential measurements in a stream of fluid in close to real time and reports results. Practically, one can make in excess of 100 different measurements simply by adjusting the optical filters for both transmitting and detecting light to utilize the desired wavelength(s). As a practical matter about 10 or 20 combinations would be sufficient to detect the likely anomalies. Less common anomalies may be detected at a lower frequency than the more common components being measured. It is likely that at least 1, 2, 3, 4 or 5 optical measurements may be sufficient for routine monitoring and when one measurement appears out of the normal range, more and different types of optical measurements may be taken to better determine better the constitution of the fluid flow. The tables below exemplify 5 and 9 water components for common measurement. However these are merely an exemplified starting point with a potential of a large number of additional measurements taken when initial screening suggests it appropriate. In a typical optical filter wheel, 12 different optical filters may be used which indicates up to 144 different combinations of light wavelengths may be measured. Of course any practical number of optical filters may be used.

A wavelength selection system to be used in the present invention may use one or two optical filters or other devices such as one or two prisms, a number of different lasers or other light sources, etc. to producing one or a very small number of wavelengths or to exclude one or a small number of wavelengths such as in making a total fluorescence measurement. One choice of optical filter may be no filter at all, e.g. total light transmission/absorption.

The same optical path and flow cell are used for all of these determinations. Generally, the advantages of using the same optical path for all measurements are much preferred.

Measurements include fluorescence, transmission, absorption, phosphorescence, reflectance and/or light scatter. All of these may be performed in whole spectrum, partial spectrum or single or narrow band wavelength or a combination of different single (or narrow) band wavelengths.

While commonly referred to as light, the spectrophotometric measurements may be performed on wavelengths outside the range of visible light. For the purposes of this application, "light" includes all other wavelengths, particularly those in the ultraviolet and near infrared ranges.

Substances detected span the range of chemical, geochemical and organic contaminants. Such examples include nitrate, chlorophyll-turbidity, total organic carbon (TOC), pesticides, hydrocarbons, and airplane deicer fluids.

Measurements across the same optical path permit a good comparison of the ratios of different spectrometric signals, which in turn provide a good indicator of biogeochemical changes in the fluid stream.

The invention makes certain baseline measurements that are fundamental to water quality in natural waters and others that can be used to make corrections for interferences on the analytical signals.

| Abbreviation | Measurement type | Typical material being measured |
| --- | --- | --- |
| HF | Humic fluorescence | Calibrated to total organic carbon |
| UV254 | Absorption in the ultraviolet | Aromatic compounds Basic water quality parameter |
| TRANS | Light transmission | Measure of turbidity |
| RF | Raman scattering | Measure of turbidity |
| R600 | Reflectance at 600 nm | Measure of turbidity |
| NO3 | Adsorption at 220 nm | Nitrate - Macronutrient |
| TF | Total fluorescence (high energy fluorescence) | Many organic compounds |
| CHL-A | Fluorescence –685 nm | Chlorophyll-a Product of plants/algae growth |
| BAC | Ultraviolet fluorescence | Related to bacteria |

Many other substances may be monitored such as volatile organic compounds (VOCs), bromide, iron—basically any substance that absorbs, fluoresces, or scatters light between 190 and 900 nm.

General categories of contaminants or components may be determined or by judicious selection of wavelengths, a class of compounds or even a single specific compound may be detected. Examples of classes or types of compounds include: cyclic organics, inorganics, particles, chlorine/chlorinated/halogenated compounds etc. More specific classes of compounds may also be determined such as ketones, aromatics, carboxylates etc.

In the invention, measurements can be recorded during a programmed sequential scan of photometric transmissions and detections. During each measurement the bandwidth of the optical filter for the flash lamp need not be the same as that for the photodetector. In the instance of detecting fluorescence or phosphorescence, the center wavelength of the optical filter in front of the detector will be different. Filters pass more light than other devices used for selecting wavelength. Greater throughput of photons becomes critical in the measurement of natural organic matter that has low fluorescence efficiency and is thus hard to activate.

Because of the short time period needed for a flash from a flash lamp and the even less time needed for detection, many measurements may be made in a relatively short period of time. Analytical wavelengths can be changed rapidly using a filter wheel or a gradient on a movable sheet, tape or slide. These features yield a large number of measurements (>100), which can be made in less than a few minutes where each measurement may be for a separate component in the fluid stream. Thus, all of these components may be measured continually on-line in a flowing stream in almost real time.

The preferred light source is a xenon flash lamp, which emits both white light and ultraviolet light. Should it be desirable to transmit a wavelength of light, which is outside the spectrum of light emitted from any particular flash lamp, one may use multiple filaments or multiple flash lamps together or separately, preferably through the same optical fibers. While exemplified by a flash lamp, light emitted by other sources may be acceptable. In particular LEDs may be used if of sufficient power. Also, a steady light source may be used with a changing lens aperture or moving mirror to provide the flash of light through the spectrophotometer. Rotating or spinning mirrors are also preferred as a method for making many short pulses of light. These are known per se from very different optical devices, and may be used in the present invention as an alternative to flash lamp based equipment as the light source. One or more lasers may be used as a light source provided that they can emit at the desired wavelength.

The advantages of using multiple measurement techniques may be superior to a conventional single measurement technique. For example, in the context of a water system, turbidity is a function of particle size distribution and particle composition. While simple turbidity measurements offer useful information, one may also use or detect different wavelengths to measure different types of particles. Knowing the composition of the mixture of particles may offer certain advantages. At a minimum, by measuring turbidity at different wavelengths, one has an extra check on the instrument. When combined with additional multiplexed measurements as used by the present invention, a more accurate measure may be made.

Also, if a particular combination of wavelengths is used for one second, one may wish to take 50 measurements and average the results as quick measurements of short duration may be more affected by scatter. Other fluid components being measured may likewise be affected and therefore it is desirable to average multiple measurements to give a better reading. On the other hand, one may discard data from one or a few of the 50 measurements. If an air bubble or debris passes through the system, the measurement taken at that moment will be far different from the other measurements and represent a false measurement rather than a true reflection of the passing fluid. In such a situation, it may be preferred to discard certain outliers rather than average them. This type of data correction is not readily performed by simple averaging or when one takes one long measurement over 50 seconds rather than 50 one-second measurements.

By comparing certain measurements, one can target the system to detect particle, biological and/or chemical contaminants, which is useful for real-time event detection. Such data may be processed in real time for immediate reporting and optional feedback modification of upstream fluid handling and processing. The immediate reporting of results also is well adapted for continuous monitoring of the fluid flow.

The present invention may be used to calculate and display or report a number of parameters for indexing water quality and highlighting anomalous chemical composition. For example, SUVA (UV254/TOC) can easily be calculated and has been considered to be an indicator of the aromaticity or degree of conjugation of the organic compounds in solution. Aromatic and conjugated compounds are commonly found in herbicides and pesticides and are structurally distinctly different than the more straight chained humic and fulvic acids that make up natural organic matter. Ring structures typically adsorb strongly in the ultraviolet spectrum and also have higher fluorescence efficiency than natural organic matter. As an additional measurement, the amount of "total fluorescence" or fluorescence activated by energetic deep UV radiation can also be used as a measure of more complex structures when the measurements are corrected by the background of total organic matter. This permits an alternative way for measuring the same type of substances, providing a good internal check for the system and greater confidence in the results reported.

More detailed analysis afforded by the present invention making dozens of different measurements also permits accurate optical measurements which would not otherwise be possible. For example, measuring an interfering component allows one to correct analytical signals, which leads to more accurate results. This may be best done in the data analysis automatically by an algorithm to compensate or to flag the measurement as being questionable.

Using the example of a turbidity measurement, suspended particles provides effects on absorption signals which are different from the effects on fluorescence signals because in absorption the light originates at the fiber assembly whereas in fluorescence the emitted light originates within the excited volume of the flow cell. This hinders quantitative measurements. By measuring the scattering of Raman fluorescence and white light transmission, the present invention is capable of making both corrections resulting in better optical quantities. Further, the output from the present spectrophotometer is in photons with its signals directly related to optical efficiencies rather than a simple analog measurement. Analog measurements such as current and electrical resistance provide lower specificity as to fluid components. While chemical sensors, such as electrodes, may be specific but these require frequent calibration and cleaning.

Measured and calculated parameters can be combined with temperature and other physical parameters, such as to identify different water types in complex solutions, such as river water or other complex mixture of primary runoff, groundwater, and/or other multiple point sources for the water. The measurement of temperature by an independent sensor is also useful for water typing.

When water-typing rivers etc, one will also measure parameters related to the time of day, date (season), and current and/or recent weather. Man-made events may also be considered such as the water quality downstream from a slaughterhouse may be different on a weekend or a holiday than on a workday. These factors may be entered into a matrix of data or used to form a different matrix to affect the acceptable ranges. For example, river water is typically more turbid after a heavy rain, algae growth is heavier during sunny summer months and many less common components are found in waters having runoff after an extended dry spell. All of these factors may be considered in determining what appropriate course of action should be taken.

The present invention can measure parameters alone or in combination to calculate other parameters. Also, it is desired for the same fluid component to be measured by 2 or more different wavelengths when practical to provide an internal check. Also, should an interfering compound be present which interferes with one of the optical measurements, it may not interfere with a different wavelength of the same fluid component. The results would be inconsistent which also indicates that an anomaly may be present.

Concentration(s) of fluid component(s) can be reported and compared to predetermined limits for automated diversion and removal of unwanted fluid components or to ensure the presence of desired fluid components (e.g. fluoride) for downstream use.

The invention may be used as a first-alert system for informing operators and or for retrieving fluids in the flow for separate detailed off-line analysis. As such, the present invention need not identify the exact abnormality or problem, but rather provide a screening tool for further analysis.

A preferred goal of the present invention is to detect biogeochemical anomalies in water flowing through a pipe. First the background character of the fluid is analyzed and cataloged for comparison purposes. The system then uses a series of fault and parameter checks to determine the nature of any anomaly detected. Most water quality parameters are periodic (e.g. changing with the time of day). Other changes reflect the season, length of day or other external factors. These changes may reflect changing microflora, nutrients and sunlight. Accordingly, a simple detection of a certain parameter concentration is not sufficient to determine whether or not an anomaly is present. The present invention measures many parameters and compensates for normal and expected background changes so as to reduce the rate of false positives and false negatives in detecting an event anomaly. As measurements of background parameters change with time, and/or instruments drift or become fouled, new base parameters are being determined or calculated and stored from which comparisons are made to test results in order to detect an anomaly in the fluid.

In the prior art, multiple different sensors may be used on a sample of fluid being tested. Each individual sensor has its own drift and separate schedule of cleaning and calibration. With the present invention, all or almost all measurements are made with the same spectrophotometer apparatus and thus all might be expected to drift together. While this affects specific concentration measurements, the ratios between various optical measurements would be less affected and therefore the present invention is less likely to miss an anomaly in the fluid flow. Additionally, since the spectrometer can take a large number or measurements, some may be dedicated to detecting instrument drift or fouling and when the measurements are outside an acceptable range, a cleaning or calibrating solution may be passed through the fluid flow in lieu of the normal fluid flow in order to correct drift or remove fouling from the instrument.

The frequency of each measurement depends upon the total number of channels and the dwell time on each channel. For example, the flash rate of the lamp could be set for 25 Hz and data collected at each measurement for 10 seconds. If it takes 5 seconds to change filters then each measurement produces 250 determinations and consumes 15 seconds. If the invention is set up to make 10 measurements, then each measurement can be repeated every 150 seconds. These times would yield optimal precision. Single measurements at lower precision can be obtained at least 50 times per second.

The invention is configurable to suit the monitoring situation. The following list shows typical measurements with their operating parameters that could be made at a water treatment plant.

Water Treatment Plant

| Parameter | Technique-Wavelength | Property |
| --- | --- | --- |
| nitrate + nitrite | absorption –220 nm | macronutrient |
| pesticides | absorption –254 nm | contaminant |
| turbidity | transmission-white light | suspended particulate matter |
| total organic carbon | fluorescence –320 nm | natural organic matter |
| chlorophyll-a | fluorescence –685 nm | algae |

The configuration at an airport where the main goal was to monitor airplane deicer fluid (ADF) could be quite different. In this case the measurements would include the determinations of glycols by absorption in the deep UV as well as absorption by anticorrosive additives and color agents at higher wavelengths. Such measurements could yield information on the types and amounts of ADF flowing past the monitoring station with time. If concentration exceeded a predetermined amount the invention could through a valve that would divert flow to a holding tank. Such a monitoring system would divert only those waters seen to be harmful. Dwell times at this case could be kept short to maximize the amount of ADF diverted for recycling.

It is an embodiment of the present invention to present a new instrument with capabilities different from similar analytical instruments in the past. The system preferably has only one device having a single optical path and flow cell making many separate optical measurements. In this system, essentially every photon is accounted for and the optically determined ratios from each wavelength or group of wavelengths are measured with minimal scattering. Most artifacts in measurements from the system are common to many measurements and are canceled out when measurements from the same technique are normalized to each other.

The present system provides the speed of optical measurements and sensitivity of spectrophotometry over many wavelengths as well as the low maintenance of a single flow cell. The goal of the present invention is to take many different types of measurements with a single system and to use data mining and analysis techniques to determine the meaning of a large number of measurements of various different types.

The sensor system is depicted in FIG. 1 where the flow cell 1 contains the portion of fluid being analyzed at any given moment. Fluid from a source to be analyzed has at least part of its flow pass in inlet 2 through the inlet line 8 to flow cell 1 and to outlet 3 which may be either a drain or recombined with the fluid flow. Valve 4 regulates the flow rate of fluid through the flow cell, particularly if the flow is to be intermittent or reduced at certain times. A temperature sensor 5 is placed in or in the vicinity of the flow cell 1 to accurately determine the fluid temperature at the time of monitoring. When needed, cleaning solutions, calibrating solutions, standards and chemicals or other components to be added to the fluid flow are provided in one or more vessels 6 connected by a line 7 to the inlet line 8. The addition is controlled by flow valve 9. When multiple vessels 6 are present, each may have its own line and valve, which independently enter to inlet line 8 or enter into line 7 either before or after flow valve 9 (not shown). Optical components and electronics 10 are optically connected to the flow cell through an optical fiber assembly 11.

A detailed depiction of the optical components is shown in FIG. 2. The flow cell 1 is shown having a flow cell inlet 19 and flow cell outlet 20. An optical emitter system 21 preferably contains at least a flash lamp 22. Light is shined through optical filter 24 to select a desired wavelength (s) and passes into and through an optical fiber or bundle of transmitting optical fibers 23 and into the flow cell 1 or optionally through a combined optical fiber 27 before the flow cell 1. The light is then shined through the fluid and reflected of a reflector 25 through the fluid again and into the optical fibers. One suitable reflector has previously been described as a "moonbeam lens" and consists of a ball lens in a semi-reflective cradle. The optical fibers may either be split to form a returning optical fiber 26 or the returning optical fiber(s) 26 may be fused to or among the transmitting optical fiber(s) 23. The returning optical fiber shines light through another optical filter 28 and is detected by optical detector 29.

The entire system should be inert to the fluids flowing through it. The entire system should preferably be self-priming without air bubbles becoming trapped inside. The entire system should permit laminar fluid flow through the flow cell or at least across the region where light is passed.

The optical fiber may preferably be a large number of fused silica light guides to maximize signal throughput and minimize background. The reflector may preferably be a moonbeam lens. Each optical filter may be a filter wheel and may be separately controllable or linked either mechanically or controlled electrically so that the same or a particular desired wavelengths of light are transmitted and received.

The combined optical fiber 27 and/or the reflector 25 may have a lens for concentrating light and/or focusing light on each other. The lens may be spherical or hemispherical and may be made of fused silica that may be polished.

The optical detector is any device that responds to and preferably measures light intensity. For example, a photomultiplier tube which converts the light signal into digital form for processing. The optical detector is preferably has a photon counting detection module with a photon stop to isolate the detector from stray photons and protect it from electromagnetic pickup. The detector should preferably be shielded from the lamp source by a plate of soft metal. Preferably, a bright image configuration to maximize signal and minimize stray light should be used. Ideally, every photon should be accounted for.

Each moving part may be physically linked or electrically controlled independently. Signals from a programmed general-purpose computer or a specialized computer control movement of valves, optical filter wheels, etc. Signals from the optical detector 29 are received, recorded and analyzed by a computer and the results reported or signals are emitted to affect appropriate change in the sensor system or fluid control system as a feedback loop.

For convenience, the entire sensor system may be included in a single integrated system, optionally contained within a single container such as a wall-mounted box with a hinged door for easy access.

The flow cell may have a programmable valve system at the inlet that would allow for access to multiple source fluids, or to drain the flow cell. This feature gives the present invention the capability to monitor multiple source fluids and report the quality control information for each as well as to flush the system with clean water or other standardized fluid between different fluid flows. The changing of fluids being monitoring may be automatic based on a preprogrammed set of parameters, responsive to a measurement taken or manually as desired or for maintenance purposes. The valve system also allows the flow-cell to be drained at programmable intervals and subsequent readings used as an internal system check. If these readings indicate substantial signal degradation they can be used to adjust subsequent calculated values as dictated by predetermined algorithms.

A temperature sensor may be inside the flow cell or close to the inlet or outlet of the flow cell to determine the temperature of the fluid being analyzed. A thermistor is a typical temperature sensor.

While exemplified by using portions of the same optical fiber for both transmitted and received light, one may also use two separate optical fibers. In such a situation, the reflector reflects light to a different location where the receiving optical fiber is located. This arrangement is particularly beneficial when detecting a fluid with a change in its index of refraction such as a change in composition in a fluid resulting from chemical processing. Alternatively, the receiving optical fiber may be in the location of the reflector, thereby avoiding the need for a reflector.

Even though the present invention is most conveniently practiced with optical fibers, one may avoid the use of one or both optical fibers altogether by having the transmitting light source or receiving light source be attached to the flow cell directly.

The preferred method is to construct a model of the data set collected over a period of time, where the model is dependent on the date and time as well as the parameters for the near past (1, 5, 10, 20 minutes ago etc.). The outputs of the model are predictions for the behavior of these parameters. If the new readings vary by some select amount from the expected result, an anomaly may be concluded and operators are alerted to switch controlling valves to prevent the anomalous fluid from being passed downstream. Alternatively, the switching of controlling valves may be automatic. The type and degree of valve switching to divert the fluid or to add compensating chemicals (such as chlorine) may be performed automatically.

It is another embodiment of the present invention that from the output from the various measurements, one can deduce specific contaminants, changes or effectiveness of the upstream processing. Algorithms may be used to extract useful information from the mass of raw data. One algorithm exemplified above is the simple ratio of UV254/TOC. Additional specific algorithms may be based on experimental systems where selective different waters or differing concentrations of different water components are added and the resulting effects on the monitoring station measured. Alternatively, when the present invention has been in use monitoring fluid flow and a known change in the fluid occurs, one may review recorded data and deduce that certain previously detected changes in the measurements are indicative of the known change in the fluid.

Measurements are optical or electrical in nature, which provides real-time analysis and an almost simultaneous determination of the water's qualities. Measurements may also be plotted against time to provide later off-line analysis, quality control or historical records. The upstream processing may be altered according to the monitored results. Furthermore, should the monitored stream be unacceptable, it may be removed and held, further processed or discarded until the parameters in the water stream are acceptable. The results may be used equally for a screening of acceptable water as well as a feedback loop adjustment of upstream operations for efficient and effective plant operation.

Typically, the sum total of the measurement data is placed in a matrix and a large number of ratios between fluid components may be compared. While many combinations do not provide useful information, many others may be utilized. The specific component measurements and ratios between measurements of interest will vary with the type of fluid being tested, the predicted or likely components and contaminants may be preset into a computer to report the results. The computer may be either a general-purpose computer appropriately programmed or a specialized device designed for the purposes of the present invention. Anomalous readings may also be determined empirically or experimentally with the results stored in the computer as an anomalous result.

The acceptable ranges may be based on a) a predefined range or b) a ratio between plural data is compared to a predefined range or c) the result from an algorithm applied to plural data is compared to a predefined range. Acceptable ranges may also be determined experimentally by reviewing past data. Acceptable ranges may also be modified according to other normal changes occurring in the fluid flow as mentioned above.

Ultimately, the computer should store an acceptable range for each component and an acceptable range for each ratio of interest. Furthermore, it is desirable to store unacceptable ranges, which are indicative of known problems.

The data values from the matrix may be manipulated in a large number of ways including generating an algorithm using one or multiple data from the various spectrophotometric measurements. The final result may provide a more accurate determination of the anomaly or contamination you are looking for. Because each of the data were obtained from the same equipment, if an equipment problem or drift occurs it is less likely to give a false reading than relying on a single spectrophotometric measurement.

The resulting data and analysis provides a matrix of measured and calculated values, which can then be used to detect events in the water flow such as contamination and anomalies in the biogeochemical composition of the fluid. These anomalies can signal real events of interest such as in the example of a water treatment situation, agricultural influx, industrial drainage, release of water from dams, controlled tributary streams or lakes, floods, punctuated erosion, etc.

All systems may be controlled and monitored by Labview software or the like. The user specified parameters may be calculated from measured quantities or empirically determined and displayed in real time.

It is also preferred to have software perform parameter calculation and to plot the results.

Modeling software having algorithms based on time-resolved multivariate regression modeling is preferred. Such systems have been previously described.

The results from many sensors may be monitored at a centralized location and appropriate action taken throughout the fluid distribution system. A supervisory control and data acquisition (SCADA) like system may receive sensor data from multiple fluid distribution systems, particularly if some are overlapping in function. This is particularly useful for region wide fluid distribution systems such as natural gas, petroleum pipelines, water systems (agricultural, drinking, sewage, etc.), chemical processing plants, etc. With such information, a feedback loop of changes may be effected.

The present invention is designed to be practical not only in natural, industrial, agricultural, drinking and waste water systems but also for industrial systems. Industrial systems include food and beverage manufacture as well as waste stream monitoring. The fluid components being detected or measured also provide verification of quality starting substrate(s), quality intermediate(s) a quality final product(s) in any type of fluid process.

As an example of monitored fluid systems, at an airport, antifreeze and deicing liquids (typically containing ethylene glycol and the like) are sprayed on airplanes. The fluid flowing off contains water as well as the deicing fluid. It is desirable to recover the deicing fluid that is not too dilute for recycling and to prevent pollution or even a toxic waste disposal situation. In this situation, the fluid running off the plane is monitored for deicing components and/or water and/or other grime that builds up on airplane wings. The fluid flow off the wings is collected and flows through a pipe with at least part of the stream passing through the spectrometer of the present invention to measure the various components. The output is then compared to preset parameters and the fluid flow diverted to either recycling, waste treatment or for other purposes. The comparison and feed back commands to various valves controlling fluid flow may be performed automatically by a computer or entirely or partially controlled by an operator.

It will be understood that various modifications may be made to the embodiments disclosed herein. Therefore, the above description and drawings should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

| Apparatus chart | |
|---|---|
| 1. | flow cell |
| 2. | inlet |
| 3. | outlet |
| 4. | valve |
| 5. | temperature sensor |
| 6. | vessels |
| 7. | line |
| 8. | inlet line |
| 9. | flow valve |
| 10. | optical components and electronics |
| 11. | optical fiber assembly |
| 12. | |
| 13. | |
| 14. | |
| 15. | |
| 16. | |
| 17. | |
| 18. | |
| 19. | flow cell inlet |
| 20. | flow cell outlet |
| 21. | optical emitter system |
| 22. | flash lamp |
| 23. | transmitting optical fibers |
| 24. | optical filter |
| 25. | reflector |
| 26. | returning optical fiber |
| 27. | combined optical fiber |
| 28. | another optical filter |
| 29. | optical detector |

What is claimed is:

1. An optical sensor for determining multiple optical parameters of a fluid flowing through the sensor comprising;
   a flow cell having a fluid inlet, fluid outlet and a light path that passes through a portion of the fluid in the flow cell,
   a light emitting system,
   a wavelength selection system for sequentially selecting a plurality of particular wavelengths of light from the light emitting system,
   a fiber optical system for transmitting light from the light emitting system to the light path, through the fluid and receiving light from the fluid flowing through the flow cell,
   an additional wavelength selection system for sequentially selecting a plurality of particular wavelengths of light returning from the flow cell, and
   an optical detector for detecting each of the plurality of particular wavelengths of light being received.

2. The optical sensor of claim 1 further comprising a light reflector for reflecting light which has passed through the fluid back to the same fiber optical system.

3. The optical sensor of claim 2 wherein light passes both ways through a portion of the same optical fibers in the optical fiber system.

4. The optical sensor of claim 1 wherein measurement data from a plurality of measurements is sent to a computer from the optical detector, wherein at least one measurement is different from another measurement by either a) a different wavelength of light being shined to the light path or b) a different wavelength of light being received by the optical detector.

5. The optical sensor of claim 1 wherein the wavelength selection system or the additional wavelength selection system comprises a plurality of optical filters.

6. The optical sensor of claim 5 wherein the plurality of optical filters are on a filter wheel.

7. The optical sensor of claim 4 wherein the plurality of measurements are taken on the same sample.

8. A method for monitoring a fluid for contamination comprising:
   continuous flowing fluid through a detection cell and across a light path,
   spectrophotometrically measuring an optical feature of the fluid in the light path,
   spectrophotometrically measuring a different optical feature of the fluid in the light path, wherein either a different wavelength of light is shined to the same light path or a different wavelength of light is detected from the fluid in the same light path.

9. The method of claim 8 wherein the optical feature of the fluid and the different optical feature of the fluid are both indicative of a same component in the fluid.

10. The method of claim 9 wherein the component is a compound.

11. The method of claim 8 wherein each optical feature is an absorption, fluorescence or reflectance measurement.

12. The method of claim 8 wherein data from spectrophotometric measurements is sent to a computer.

13. The method of claim 12 wherein the data is compared to a) a predefined range or b) a ratio between plural data is compared to a predefined range or c) the result from an algorithm applied to plural data is compared to a predefined range.

14. The method of claim 11 wherein said optical feature and said different optical feature are not both absorption or not both fluorescence or not both reflectance.

15. A method for determining whether a fluid stream contains an anomalous composition comprising;
   continuous flowing fluid through a detection cell and across a light path,
   spectrophotometrically measuring a first optical feature of the fluid in the light path by an instrument,
   spectrophotometrically measuring a different optical feature of the fluid in the same light path by the same instrument, wherein either a different wavelength of light is shined to the same light path or a different wavelength of light is detected from the fluid in the same light path,
   generating an algorithm using plural data from plural spectrophotometric measurements from the same equipment, to give a resulting value,
   comparing the resulting value to a predefined range to determine whether the measurements indicate the presence of an anomalous composition in the fluid, and
   reporting the results.

16. The method of claim 15 wherein the predefined range is modified based on at least one spectrophotometric measurement.

17. The method of claim 16 wherein the predefined range is modified based on an algorithm from at least two spectrophotometric measurements.

18. The method of claim 16 wherein the results indicates the presence of a particular compound or class of compounds in the fluid.

19. The method of claim 16 further comprising modifying the predefined range based on external factors which are expected to modify the composition of the fluid.

* * * * *